United States Patent [19]

Bertleff et al.

[11] Patent Number: 4,910,328

[45] Date of Patent: Mar. 20, 1990

[54] PREPARATION OF OMEGA-FORMYLALKANECARBOXYLIC ESTERS

[75] Inventors: Werner Bertleff, Viernheim; Robert Maerkl, Fussgoenheim; Michael Roeper, Wachenheim, all of Fed. Rep. of Germany

[73] Assignee: BASF Akteingesellschaft, Ludwigshafen, Fed. Rep. of Germany

[21] Appl. No.: 206,752

[22] Filed: Jun. 15, 1988

[30] Foreign Application Priority Data

Jun. 15, 1987 [DE] Fed. Rep. of Germany ........ 3719938

[51] Int. Cl.$^4$ ............................................. C07C 69/66
[52] U.S. Cl. ..................................................... 560/177
[58] Field of Search ......................................... 560/177

[56] References Cited

U.S. PATENT DOCUMENTS 3,253,018 6/1966 Zachry et al. ...................... 560/177

FOREIGN PATENT DOCUMENTS 0125567 3/1984 European Pat. Off. .
173226 3/1986 European Pat. Off. .
1586805 3/1981 United Kingdom .

OTHER PUBLICATIONS

C. R. Acad. Sc. Paris, t. 272(1971) pp. 86–88.
Chemiker–Zeitung, 1976,718, p. 309.

Primary Examiner—Paul J. Killos
Attorney, Agent, or Firm—Keil & Weinkauf

[57] ABSTRACT

ω-Formylalkanecarboxylic esters are prepared by hydroformylation of an alkenecarboxylic ester with carbon monoxide and hydrogen at elevated tempertures and under superatmospheric pressure in the presence of a cobalt carbonyl complex by a process in which an α,β-unsaturated alkenecarboxylic ester is hydroformylated in the presence of from 0.01 to 1 mol %, calculated as cobalt, of a cobalt carbonyl complex, while maintaining a conversion of from 10 to 70% of α,β-unsaturated alkenecarboxylic esters.

6 Claims, No Drawings

PREPARATION OF OMEGA-FORMYLALKANECARBOXYLIC ESTERS

ω-Formylalkanecarboxylic esters are desirable starting materials for the preparation of ω-aminocarboxylic acids, which are monomers for the preparation of polyamides. European Patent Application 125,567 discloses that 3-pentenoic esters are first isomerized to 4-pentenoic esters and then hydroformylated and hydrogenated in order to obtain 6-aminocaproic esters. However, the isomerization is a technically complicated step.

The hydroformylation of $\alpha,\beta$-unsaturated alkenecarboxylic esters in the presence of cobalt catalysts is also described in C.R. Acad. Sci. Ser. C 272 (1971) 1, pages 86–88, where methyl 3-methylbut-2-enoate is reacted with a mixture of carbon monoxide and hydrogen at 140° C. and under 180 bar using cobalt octacarbonyl as a catalyst. 3-Methyl-4-formylbutyrates are obtained in a yield of 72%. The remainder is the hydrogenation product methyl isovalerate. The hydrogenation is said to be an unavoidable side reaction.

Furthermore, the hydroformylation of methyl 2-hexenoate in the presence of cobalt octacarbonyl is described in Chemiker-Zeitung 1976, Part 7/8, page 309. The reaction is carried out in a very dilute solution in benzene at 90° C. and under 140 bar. This method gives only 53% of straight-chain methyl formylhexanoate. Furthermore, it is expensive to use large amounts of solvent.

U.S. Pat. No. 3,253,018 describes the hydroformylation of mixtures of isomeric pentenoic esters in the presence of cobalt catalysts to give formylvaleric esters. This publication states that 2-pentenoic esters are not very suitable for the preparation of 5-formylvaleric esters since they have the slowest reaction rate and tend to undergo polymerization. However, owing to conjugative effects, $\alpha,\beta$-unsaturated alkenecarboxylic esters are the most stable and most readily obtainable by isomerization. They did not appear to be suitable for the preparation of ω-formylalkanecarboxylic esters.

It is an object of the present invention to prepare ω-formylalkanecarboxylic esters starting from $\alpha,\beta$-unsaturated alkenecarboxylic esters by hydroformylation, without prior isomerization, and to reduce the amount of byproducts obtained.

We have found that this object is achieved by a process for the preparation of ω-formylalkanecarboxylic esters by hydroformylation of alkenecarboxylic esters with carbon monoxide and hydrogen at elevated temperatures and under superatmospheric pressure in the presence of a cobalt carbonyl complex, wherein an $\alpha,\beta$-unsaturated alkenecarboxylic ester is hydroformylated in the presence of from 0.01 to 1 mol %, calculated as cobalt, of a cobalt carbonyl complex while maintaining a conversion of from 10 to 70% of the $\alpha,\beta$-unsaturated alkenecarboxylic ester.

The novel process has the advantage that the expensive step, prior to the hydroformylation, for isomerization to give alkenecarboxylic esters unsaturated at the chain end is avoided and $\alpha,\beta$-unsaturated alkenecarboxylic esters are used as starting materials. Another advantage of the novel process is that the formation of by-products is reduced.

The starting compounds used according to the invention are $\alpha,\beta$-unsaturated alkenecarboxylic esters, in general $\alpha,\beta$-unsaturated $C_4$–$C_6$-alkenoic esters which are preferably derived from alkanols of 1 to 12 carbon atoms or cycloalkanols of 5 to 8 carbon atoms. Straight-chain $\alpha,\beta$-unsaturated $C_6$–$C_6$-alkenoic ester of alkanols of 1 to 4 carbon atoms are preferably used as starting materials. Examples of suitable starting compounds are methyl, ethyl, propyl, butyl, hexyl, octyl, cyclopentyl and cyclohexylcrotonate, 2-pentenoate and 2-hexenoate. 2-pentenoic esters have become particularly important industrially as starting materials.

The hydroformylation is carried out at elevated temperatures, advantageously at from 60° to 130° C., in particular from 80° to 110° C., under superatmospheric pressure, advantageously from 50 to 200, in particular from 30 to 180, bar. As a rule, the gas mixture contains carbon monoxide and hydrogen in a molar ratio of from 1:0.5 to 1:10, in particular from 1:1 to 1:2.

The hydroformylation is carried out in the presence of a cobalt carbonyl complex. Cobalt octacarbonyl which is converted into the catalytically active compound under the reaction conditions is advantageously used. On the other hand, it is also advantageous to produce the catalytically active cobalt carbonyl complexes in situ from cobalt salts of fatty acids, for example cobalt acetate, formate, propionate or butyrate. Other suitable starting compounds for the preparation of suitable catalysts are cobalt oxides and cobalt in metallic form. Another preferred form is obtained by preparing cobalt hydrogen carbonyl in aqueous solution by treating cobalt salt solutions with a mixture of carbon monoxide and hydrogen and then extracting cobalt hydrogen carbonyl, advantageously with the alkenecarboxylic esters used as starting materials.

The hydroformylation is carried out in the presence of from 0.01 to 1, preferably from 0.05 to 0.3, in particular from 0.08 to 0.25, mol %, calculated as cobalt and based on the $\alpha,\beta$-unsaturated alkenecarboxylic esters used, of cobalt carbonyl complexes. It is also essential with regard to the invention to maintain a conversion of from 10 to 70%, preferably from 15 to 50%, in particular from 20 to 40%, of $\alpha,\beta$-unsaturated alkenecarboxylic esters. This gives a selectivity of about 70% of ω-formylcarboxylic esters, and only 4–5% of hydrogenation products and high boiling components are obtained.

After the pressure has been let down, the hydroformylation mixture is worked up by a conventional method. A suitable method is described in, for example, European Patent 31,100. In this method, the pressure is let down and the hydroformylation mixture discharged is then treated with an oxidizing agent, such as hydrogen peroxide or a gas containing molecular oxygen, in particular air, advantageously in an amount of from 2 to 10 oxidation equivalents per mole of cobalt catalyst, in the presence of an aqueous acidic solution, for example aqueous formic acid, acetic acid, butyric acid, valeric acid or 2-ethylhexanoic acid, at, for example, from 80° to 160° C., in particular from 100° to 130° C. Depending on the degree of mixing, the cobalt catalyst separates out completely after only a few seconds or fractions of a second. The cobalt-containing aqueous phase is advantageously separated off by decanting and is reused for the preparation of the catalyst. ω-Formylalkanoic esters are isolated from the resulting organic phase by distillation, and unconverted $\alpha,\beta$-unsaturated alkenecarboxylic esters are recycled to the hydroformylation.

The Examples which follow illustrate the process according to the invention. PSE is methyl pentenoate, FVSE is methyl formylvalerate, HSE is methyl hexenoate and FHSE is methyl formylhexanoate.

EXAMPLES 1 (COMPARISON) AND 2

The experiments were carried out in a continuously operating apparatus having a liquid metering pump, by means of which the methyl pentenoate and the dissolved cobalt catalyst were conveyed to the 2 stirred autoclaves connected in series. The synthesis gas was introduced together with the liquid feed upstream of the first reactor, the pressure being regulated. The two reactors had liquid volumes of 1.2 and 1.12 l, respectively. The two-phase discharged mixture was collected under superatmospheric pressure in a container, from which a certain amount of waste gas was released via a regulating valve. The liquid phase was let down into a receiver, the level being regulated.

$Co_2(CO)_8$ was used as the catalyst intermediate, and the hydroformylation was carried out using 1:1 $CO/H_2$. Methyl 3-pentenoate was used for Example 1, and methyl 2-trans-pentenoate for Example 2. The reaction was carried out at 100° C. and under 90 bar using a space velocity of 0.15 $l \times l^{-1} \times h^{-1}$.

| Example | $\frac{\text{Mole of Co}}{\text{Moles of PSE}} \times 100\ [\%]$ | % Conversion | % n content[1] | % Select. for 5-FVSE |
|---|---|---|---|---|
| 1 (Comparison) | 0.16 | 32.8 | 68.7 | 67.9 |
| 2 | 0.16 | 49.9 | 72.2 | 69.2 |

[1]Content of 5-formylvaleric ester (5-FVSE) in total amount of formylvaleric esters

EXAMPLES 3 (COMPARISON) AND 4

These experiments were carried out in a 2.5 l lift-type stirred autoclave. 340 g of methyl 3-pentenoate (Example 3) or 340 g of methyl 2-trans-pentenoate (Example 4) and 0.79 g of $Co_2(CO)_8$ (0.16 mol % of cobalt) were initially taken. The reaction was carried out under from 75 to 80 bar at 100° C. using 1:1 $CO/H_2$. The progress of the reaction was determined by taking samples after 90, 210, 280 and 340 minutes. The attached Figure shows that methyl 2-trans-pentenoate is hydroformylated more rapidly than methyl 3-pentenoate.

EXAMPLES 5 (COMPARISON) AND 6

These experiments were carried out similarly to Examples 3 and 4, except that methyl hexenoate was used. 340 g of the ester were employed in each case. A mixture as obtained from the cleavage of caprolactone and containing 66% of the 5-isomer, 20% of the 4-trans-isomer and 12.6% of the 4-cis-isomer was used for Example 5, and methyl 2-trans-hexenoate was used for Example 6. The cobalt concentration was 0.18 mol % and the reaction conditions were 75–80 bar, 1:1 $CO/H_2$, 100° C. and 90 minutes.

| Example | $\frac{\text{Mole of Co}}{\text{Moles of HSE}} \times 100\ [\%]$ | % Conversion | % n content[1] | % Select. for 6-FHSE[2] |
|---|---|---|---|---|
| 5 (Comparison) | 0.18 | 17.6 | 65.9 | 65.8 |
| 6 | 0.18 | 16 | 72.2 | 67.3 |

[1]Content of methyl 6-formylhexanoate in the total amount of formylhexanoic esters
[2]FHSE = methyl formylhexanoate

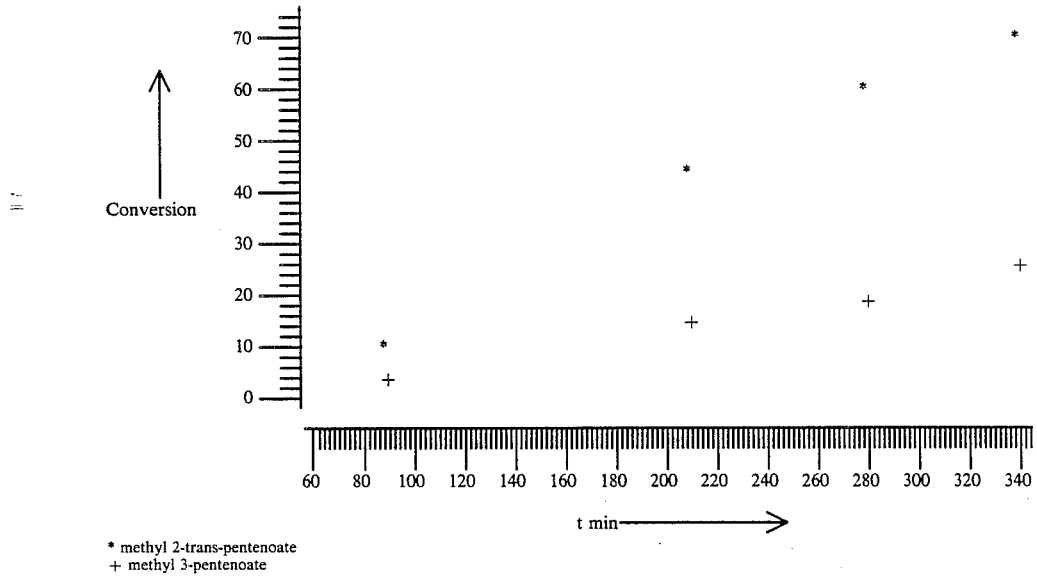

\* methyl 2-trans-pentenoate
\+ methyl 3-pentenoate

We claim:
1. A process for the preparation of an $\omega$-formylcarboxylic ester which comprises hydroformylating a straight-chain $\alpha,\beta$-unsaturated $C_4$–$C_6$-alkenoic ester of an alkanol of 1 to 4 carbon atoms with carbon monoxide and hydrogen at from 60° to 130° C. and under from 50 to 200 bar in the presence of from 0.01 to 1 mol%, calculated as cobalt and based on the straight-chain α,β-unsaturated alkenecarboxylic ester of a cobalt complex, while maintaining a conversion of from 10 to 70% of the straight-chain α,β-unsaturated carboxylic alkenoic esters used in the process.

2. The process of claim 1, wherein from 0.05 to 0.3 mol %, calculated as cobalt, of a cobalt carbonyl complex is used.

3. The process of claim 1, wherein a conversion of from 15 to 50% is maintained.

4. The process of claim 1, wherein a temperature of from 80° to 110° C. is maintained.

5. The process of claim 1, wherein a pressure of from 30 to 180 bar is maintained.

6. The process of claim 1, wherein a $C_1$–$C_4$-alkyl 2-pentenoate is used.

* * * * *